United States Patent [19]
Arnoldy et al.

[11] Patent Number: 5,968,322
[45] Date of Patent: Oct. 19, 1999

[54] PROCESS FOR PREPARING REFINED ACRYLIC ESTERS

[76] Inventors: Peter Arnoldy; Eric Kragtwijk; Antoon Paul Michael Kremers, all of Badhuisweg, 3 1031 CM Amsterdam, Netherlands

[21] Appl. No.: 08/979,264

[22] Filed: Nov. 26, 1997

Related U.S. Application Data

[63] Continuation of application No. 08/515,477, Aug. 15, 1995, abandoned.

[30] Foreign Application Priority Data

Aug. 18, 1994 [EP] European Pat. Off. .............. 94202354

[51] Int. Cl.$^6$ .............................. B01D 3/34; C07C 51/44; C07C 67/54
[52] U.S. Cl. .................................... 203/6; 203/8; 203/49; 203/65; 203/71; 203/DIG. 21; 560/218; 562/600
[58] Field of Search .................................... 203/8, 29, 33, 203/38, 64, 63, 71, 6, 65, 49, DIG. 21, DIG. 23; 560/218, 4, 206; 562/598, 600

[56] References Cited

U.S. PATENT DOCUMENTS

| | | |
|---|---|---|
| 908,001 | 12/1908 | Horbet et al. . |
| 3,666,794 | 5/1972 | Otsuki et al. ............... 203/8 |
| 3,674,651 | 7/1972 | Otsuki et al. . |
| 3,717,553 | 2/1973 | Otsuki et al. . |
| 3,812,175 | 5/1974 | Happel et al. ........... 560/206 |
| 3,816,267 | 6/1974 | Chuang . |
| 3,988,213 | 10/1976 | Yoshida et al. ............ 203/8 |
| 4,021,310 | 5/1977 | Shimizu et al. ............ 203/8 |
| 4,861,902 | 8/1989 | Haubrich et al. ........ 549/499 |

FOREIGN PATENT DOCUMENTS

| | | |
|---|---|---|
| 768651 | 10/1967 | Canada . |
| 186228 | 7/1986 | European Pat. Off. . |
| 539628 | 5/1993 | European Pat. Off. . |
| 571044 | 11/1993 | European Pat. Off. . |
| 1275644 | 10/1961 | France . |
| 2201275 | 4/1974 | France . |
| 52125116 | 10/1977 | Japan . |
| 219252 | 12/1984 | Japan . |
| 07053449 A | 2/1995 | Japan . |

OTHER PUBLICATIONS

Przem. Chem. (1982), 61(9), 304–5–"Stabilization of acrylic monomers", Y. Morawski Polish journal paper describing the effectiveness of compounds and mixtures as polymerization inhibitors in the distillation of acrylic compounds. For acrylic acid hydroquinonc, phenothiazine and inhibitors in the distillation of acrylic compounds. For acrylic acid hydroquinone, phenothiazine and air is considered most suitable with the further addition of p–methoxyphenol for methyl methacrylate.
International Search Report Nov. 8, 1995.

*Primary Examiner*—Virginia Manoharan

[57] ABSTRACT

A process for preparing refined acrylic esters, the process including steps of distilling an acrylic ester containing stream in the presence of hydroquinone or substituted hydroquinone, at a concentration in the range of 200 to 5000 ppmw, wherein the distillation is carried out in the presence of 0.001 to 1.0 % v, on the vapor phase, of oxygen.

12 Claims, No Drawings

PROCESS FOR PREPARING REFINED ACRYLIC ESTERS

This is a continuation, continuation-in-part of application Ser. No. 08/515,477 filed on Aug. 15, 1995 abandoned.

FIELD OF THE INVENTION

The invention relates to a process for preparing refined acrylic esters by distillation of an acrylic ester containing stream in the presence of a phenolic inhibitor.

BACKGROUND TO THE INVENTION

Acrylic esters can be represented by the general formula $CH_2=CR^1COOR^2$, wherein $R^1$ represents a hydrogen atom or an optionally substituted hydrocarbyl group, preferably a hydrogen atom or a methyl group and $R^2$ represents an optionally substituted hydrocarbyl group, typically an alkyl group such as a methyl group. The invention relates in particular to refined methyl acrylate and, more particularly, methyl methacrylate (hereinafter MMA).

Acrylic esters are valuable compounds that readily polymerize or copolymerize with a wide variety of other monomers. The reverse side of the coin is that it is difficult to prepare acrylic esters of sufficient purity without inadvertently converting part of the acrylic esters into oligomers, polymers or other undesirable products during their preparation.

The various methods for preparing acrylic esters are discussed in detail in volume 1 of the fourth edition of the Kirk-Othmer Encyclopedia of Chemical Technology (pp. 287–314, in particular FIG. 1 on p. 296). The same reference provides a typical process for preparing acrylic esters by esterification (pp. 301–302, FIG. 4) wherein acrylic acid, alcohol and a catalyst are fed to an esterification reactor. The esterification products (acrylic ester, excess alcohol and water of esterification) are taken overhead from the distillation column. The process uses additional wash and distillation columns to yield a refined acrylic ester. To minimize formation of the acrylic ester oligomers, polymers, etc., mild conditions and short residence times are maintained throughout the separation sections. In addition, conventional free-radical polymerization inhibitors are fed to each of the distillation columns. Finally, monomethyl ether of hydroquinone (10–100 ppmw, hereinafter MEHQ) is added to the end product as polymerization inhibitor and the esters are used in this form in most industrial polymerizations. This reference also discusses alternative routes to acrylic esters, based on acetylene, etc., that each incorporate a final (series of) distillation column(s) to separate refined acrylic ester. Indeed, as the alternative routes give rise to a multitude of difficult to separate side-products, distillation to separate refined acrylic ester is essential.

The Process Economics Program Report No. 11D, entitled METH-ACRYLIC ACID AND ESTERS" by SRI International of January, 1993, provides a further thorough review of the routes to MMA and methacrylic acid. Concerning MMA purification, suggested treatments include distillation, extraction, and treatment over ion-exchange resins or carbon beds. To avoid polymerization during purification, MMA must not be exposed to high temperatures, and distillation is generally done under vacuum and in the presence of polymerization inhibitors (pp. 5–4 to 5–5). In section 9 of the Report (MMA from propyne) it is proposed to distil under vacuum conditions to keep temperatures low and minimize decomposition or polymerization. In the Report it is suggested to add about 600 ppmw of MEHQ as polymerization inhibitor (p.9–5).

U.S. Pat. No. 4,518,462 discloses a 2 column distillation process for removing water, methanol and methyl isobutyrate from MMA by using an n-hexane entrainer. In the examples, 0.02% of hydroquinone and 0.03% of phenothiazine are used as polymerization inhibitors in the first distillation column. In the second distillation column, 5% of hydroquinone is used.

In Japan Kokai 2-17151 (1990, abstract) distillation of impure MMA in the presence of 200 ppmw 4-benzoquinone plus 800 ppmw phenothiazine is described.

Neither of these documents suggest measures to improve the efficiency of phenolic inhibitors, or identify the inhibitors used best in case the acrylic ester containing stream further comprises (the residue of) the catalyst system used to prepare the acrylic ester.

The inventors set out to determine the most optimal conditions for distillation of the acrylic ester, allowing for high throughputs by distilling at elevated temperatures, without significant loss of the acrylic ester. In particular, it is an object of the present invention to provide a process that allows distillation of the product stream of a carbonylation reaction further comprising (i) (residue of) the homogeneous catalyst system used to prepare the acrylic ester and (ii) optionally an alcohol corresponding to the alcohol residue of the acrylic ester. More in particular, it is an object of the present invention to provide a process that allows the distillation of a product stream of a carbonylation reaction catalyzed by a catalyst system based on: (a) a Group VIII metal, preferably Pd; a ligand, preferably a phosphine mono- or bidentate ligand, and (c) a source of anions (Reppe Reactions, see chapter 3 of New Syntheses with Carbon Monoxide by J. Falbe, ISBN 3-540-09674-4). Such distillations are complicated by the presence of these catalyst components as they may induce formation of the undesired oligomers, polymers etc.

SUMMARY OF THE INVENTION

These and other objects are accomplished by a process for preparing refined acrylic esters by distillation of an acrylic ester containing stream in the presence of a phenolic inhibitor, wherein the distillation is carried out in the presence of oxygen.

It has been found that the best results (least formation of acrylic ester oligomers, polymers, etc.) is obtained if the oxygen is present in an amount of 0.001 to 1.0% v (on vapor phase). If less than the preferred amount is present, some oligomerization or polymerization still occurs, whereas using oxygen in a higher concentration is undesirable for safety and economic reasons.

DETAILED DESCRIPTION OF THE INVENTION

Suitable phenolic inhibitors are known in the art and comprise for instance hydroquinone (hereinafter HQ) or 2,4,6-trimethylphenol; substituted hydroquinones such as 2,5-di-tert-butylhydroquinone, 2,5-dimethylhydroquinone, 2-methylhydroquinone, or alkyl ethers (preferably methyl ethers) of said (substituted) hydroquinone(s). Other examples are given in JP-A-05-320,095, incorporated herein by reference, wherein a process for preparing (meth)acrylic acid with alcohol in the presence of an acidic catalyst and a solvent, using as polymerization inhibitor an aromatic compound with at least one alkyl group and at least two hydroxyl groups per benzene ring. The suitability of preparing refined acrylic esters comprising distilling an acrylic ester containing stream in the presence of a phenolic inhibitor and oxygen, however, is not suggested.

Benzoquinone or similar (carbonyl) compounds, although being well-known inhibitors, are not phenolic inhibitors within the definition of the present patent application. U.S. Pat. No. 3,794,567 (incorporated herein by reference) illustrates use of polymerization inhibitors benzoquinone and hydroquinone monomethyl ether as such or in admixture in the presence of air (or oxygen) in distillation of unsaturated acids (acrylic and methacrylic acid). However, the present inventors found benzoquinone to be an unsuitable inhibitor for distillation of acrylic esters, in particular in the presence of oxygen (cf. Table 1 supra), which is in contrast to the findings of U.S. patent '567. Apparently, acrylic esters respond differently from acrylic acids to polymerization inhibitors during their distillation.

Preferably, the phenolic inhibitor is used at a concentration in the range of 200 to 5000 ppmw, more preferably in the range of 500 to 1500 ppmw (based on the acrylic ester). Using phenolic inhibitor outside the preferred range either increases the formation of the undesirable products, or merely increases the total costs.

The process is in particular suitable for preparing refined MMA. MMA and other acrylic esters may advantageously be prepared from acetone cyanohydrin, ethene, propionic acid, propionaldehyde, methyl propionate or propyne using a homogeneous catalyst system. (cf. the SRI Report mentioned before).

Hydroquinone and substituted hydroquinones are the phenolic inhibitor of preference in case the catalyst system is based on: (a) a Group VIII metal, preferably Pd; (b) a ligand, preferably a mono- or bidentate phosphine ligand; and (c) a source of anions (for suitable catalyst systems and processes for preparing such acrylic esters see, for instance, European patent applications Nos. 0,186,228; 0,190,473; 0,194,707; 0,218,283; 0,218,284; 0,386,833; 0,386,834; 0,392,601; 0,441,446; 0,441,447; 0,489,472; 0,495,547; 0,499,329; 0,521,578; 0,565,199; and 0,571,044), each of which are incorporated herein by reference.

It is observed that optimal concentration of phenolic inhibitor depends on the amount of oxygen present, and vice versa. The higher, respectively lower the concentration of phenolic inhibitor, the lower, respectively higher is the required amount of oxygen.

The distillation may suitably be carried out at vacuum or (super)atmospheric pressures using a distillation column operating at a bottom temperature of 60–140° C., preferably at a temperature in the range of 80–110° C.

Preferably the phenolic inhibitor is introduced into the distillation column together with the acrylic ester containing stream. In addition or instead, it may be introduced at or near the top of the distillation column. The oxygen may be introduced advantageously at or near the bottom of the distillation column, either by a separate inlet or through leakage in case of vacuum distillation columns.

In case the acrylic ester containing stream further comprises (i) a homogeneous catalyst system and (ii) an alcohol corresponding to the alcohol residue of the acrylic ester, it is helpful to carry out the process in two steps. For instance, in step (1) an azeotrope of the alcohol (methanol) and acrylic ester is removed over the top of a first distillation column (to be recycled if the process is part of an integrated process further comprising a reactor where the acrylic ester is produced). The first bottom product is introduced in step 2 into a second distillation column, where heavy ends (oligomers and polymers) and (the residue of) the catalyst system is removed from the refined acrylate ester from the bottom of the distillation column and the refined ester is recovered over the top of the distillation column. Other configurations, including but not limited to changing the order for removal of the azeotrope and the heavy ends, will be apparent to the man skilled in the art.

It is within the gist of the invention to use a cascade of distillation columns (in series and/or parallel) instead of using a single distillation column. A particularly suitable process for removing the azeotrope is disclosed in European patent application No. 0,571,044 and (as part of a total process) in FIG. 9.1 of the SRI report, page E-25 (incorporated herein by reference).

The invention further relates to a process for preparing refined acrylic esters by carbonylating an acetylenically unsaturated compound, preferably ethyne or propyne, with carbon monoxide and the corresponding alcohol, preferably methanol, in the presence of a catalyst system based on: (a) a Group VIII metal, preferably Pd; (b) a ligand, preferably a mono- or bidentate phosphine ligand; and (c) a source of anions, characterized in that the product stream of the carbonylation reaction is processed as set out above. Preferably, both processes are integrated such that the azeotrope stream recovered in step 1 in the two-step distillation set-up is reused. Optionally, also the catalyst system recovered from the bottom stream of the second distillation column of the two-step distillation set-up is reused.

The invention will be further illustrated by the following model examples.

EXAMPLE 1

MMA, to which 500 ppmw inhibitor was added, was kept at 80° C. under a flow of nitrogen gas or air (modelling the distillation conditions). The MMA was analyzed on the presence of ppmw PMMA (visual detection limit of 500 ppmw PMMA by observation of haziness using 2% wt MMA in methanol, determining the number of days required before PMMA could be detected). The results are set out in Table 1. From these results it may be concluded that in the presence of oxygen, the phenolic inhibitors showed improved performance, whereas the performance of p-benzoquinone decreased in the presence of oxygen. Most marked improvements were found for 2,4,6-trimethylphenol, HQ and MEHQ, although inhibitary "IONOL-K" and "IONOL-CP" (trademarks for 4-methyl-2,6-di-tert-butylphenol and 2,4-dimethyl-6-tert-butylphenol respectively) also performed well in the presence of oxygen.

EXAMPLE 2

A synthetic feed (modelling the crude product obtained in an MMA from propyne production process) comprising MMA, 100 or 1000 ppmw inhibitor, and a catalyst system comprising, if present, 40 ppmw Pd, Pd/PN/MeSA in molar ratio 1:10:5 or 1:10:20 (PN stands for 2-pyridyldiphenylphospine; MeSA stands for methanesulphonic acid) was kept at 80° C. under a flow of 0.1% v $O_2/N_2$ (modelling the distillation conditions). The feed was analyzed on ppmw PMMA (detection limit of 10 ppmw PMMA by GPC analysis). The results are set out in Table 2. From these results it may be concluded that in absence of the catalyst system, inhibitors "IONOL-CP" and "IONOL-K" perform similar to HQ and substantially better than MEHQ. However, in the presence of the catalyst system HQ performs substantially better than the other phenolic inhibitors.

TABLE 1

| Inhibitor | Stability at 80° C. under nitrogen (days) | Stability at 80° C. under air (days) |
| --- | --- | --- |
| HQ | 1 | 29 |
| 4-tert-butylcatechol | 6 | 14 |
| 2,4-di-tert-butylphenol | 1 | 16 |
| 4-methyl-2,6-di-tert-butylphenol | 2–4 | 19 |
| 2,4-dimethyl-6-tert-butylphenol | 13 | 43 |
| 2,4,6-trimethylphenol | 1 | >55 |
| MEHQ | 1 | 26 |
| p-benzoquinone | 8 | 2–4 |

TABLE 2

| Pd conc. (ppmw) | Pd/PN/MeSA (molar ratio) | inhibitor conc. (ppmw) | inhibitor type | | | |
| --- | --- | --- | --- | --- | --- | --- |
| | | | HQ | MEHQ | "IONOL-CP"* | "IONOL-K"* |
| | | | (days with < 10 ppmw or ppmw PMMA after 1 day) | | | |
| 0 | no additives | 100 | >7 days | 2 days | >6 days | >11 days |
| 40 | 1:10:5 | 100 | 4,800 | 29,000 | 17,000 | 12,000 |
| 40 | 1:10:20 | 1000 | 640 | solid only | 16000 | 19000 |

*trademarks

EXAMPLE 3

A synthetic feed comprising MMA, 100 ppmw HQ, and a catalyst system comprising, if present, 40 ppmw Pd, Pd/PN/MeSA in molar ratio 1:10:5 was kept at 80° C. under a flow of 0.1% v $O_2/N_2$. The feed was again analyzed on ppmw PMMA. The results are set out in Table 3. From these results it may be concluded that the problem of PMMA formation is particular great in the presence of the complete catalyst system.

EXAMPLE 4

A synthetic feed comprising MMA, a variable amount of HQ, and a catalyst system comprising 40 ppmw Pd, Pd/PN/MeSA in molar ratio of 1:30:35 was kept at 80° C. under a flow of 0.1% v or 20 % v $O_2$. The feed was analyzed on ppmw PMMA (detection limit of 10 ppmw PMMA by GPC analysis). The results are set out in Table 3. From these results it may be concluded that the presence of both $O_2$ and HQ are required, and that to achieve the same result in PMMA reduction either a (relatively) large amount of $O_2$ or a (relatively) large amount of HQ may be used.

EXAMPLE 5

A synthetic feed was used comprising 83.8% wt MMA, 15.1% wt MeOH, 1.0% wt methyl crotonate, a catalyst system comprising 10 ppmw Pd (fed as palladium(II) acetate), Pd/PN/MeSA in molar ratio 1:30:35 and 500 or 1000 ppmw HQ.

The feed was subjected to a two-step distillation set-up comprising two distillation columns in series, operating at the following conditions: 80–100° C. bottoms temperature; air flow in both bottoms approximately 0.3 NL (NL is a liter at 1 bar, 20° C.) per hour (0.05–0.1% v $O_2$ in vapor phase); a feed flow of 105 milliliters per hour (comprising azeotrope 25; MMA 70; heavy ends 10); and residence times in the bottoms of 3–4 hours in the first distillation column and 25–50 hours in the second distillation column.

From the results (Table 5) it may be concluded that PMMA formation may be reduced in a continuous distillation to an acceptable level. Higher PMMA levels are found in the second bottoms, due to concentration. There is only a small effect of the temperature on PMMA production.

EXAMPLE 6

Example 5 was repeated, however, with the difference that instead of a synthetic feed, crude product originating from an MMA from propyne production process was used. This feed, to which 500 ppmw HQ was added, comprised 72.7% wt MMA, 25.5% wt MeOH, 0.8% wt methyl crotonate, and catalyst system (10 ppmw Pd, Pd/PN/MeSA mole ratio 1:30:30).

The feed flow amounted to 140 milliliters per hour (comprising azeotrope 55; MMA 75; heavy ends 10). The results (Table 6) illustrate the suitability of the present process.

TABLE 3

| presence of: | | | reaction | PMMA |
| --- | --- | --- | --- | --- |
| Pd | PN ligand | MeSA | time (days) | conc. (ppmw) |
| − | − | − | 7 | <10 |
| + | − | − | 7 | <10 |
| − | + | − | 7 | <10 |
| − | − | + | 7 | <10 |
| + | + | − | 3 | 50 |
| − | + | + | 10 | <10 |
| + | − | + | 10 | <10 |
| + | + | + | 1 | 4800 |

TABLE 4

| HQ | PMMA conc. (ppmw) | |
| --- | --- | --- |
| (ppmw) | 0.1% v $O_2$ | 20% v $O_2$ |
| 50 | 7,100 | 1,600 |
| 100 | 7,100 | 40 |
| 250 | 890 | <10 |
| 750 | 80 | <10 |
| 1000 | 100 | <10 |
| 1500 | <10 | <10 |

TABLE 5

| HQ conc. | PMMA conc. in 1st/2nd column bottoms (ppmw/ppmw) | | | | | |
|---|---|---|---|---|---|---|
| (ppmw/feed) | 80° C. | | 90° C. | | 100° C. | |
| 500 | 30 | 3,100 | <10 | 1,100 | 30 | 12,500 |
| 1000 | 20 | 520 | <10 | 710 | 40 | 740 |

TABLE 6

| bottoms temperature (° C.) | air flow (NL per hour) | PMMA conc. in 1st/2nd column bottoms (ppmw/ppmw) | | |
|---|---|---|---|---|
| | | feed | 1st bottom | 2nd bottom |
| 80 | 0.5 | 820 | 1,460 | 17,600 |
| 100 | 3.0 | 820 | 1,060 | 8,900 |
| 100 | 1.5 | 820 | 1,200 | 11,000 |
| mass balance* | | 820 | 1,250 | 10,500 |

*calculated amount of PMMA present in the bottoms if no PMMA is formed, but merely concentrated.

We claim:

1. A process for preparing refined acrylic ester, the process comprising the step of distilling an acrylic ester containing stream wherein the acrylic ester containing stream comprises acrylic ester and a homogeneous catalyst system, the catalyst system is based on: (a) Pd; (b) a mono- or bidentate phosphine ligand; and (c) a source of anions in the presence of a phenolic inhibitor consisting essentially of either hydroquinone or a substituted hydroquinone, and the phenolic inhibitor is used at a concentration in the range of 200 to 5000 ppmw, wherein the distillation is carried out in the presence of 0.001 to 1.0% v, on the vapor phase, of oxygen.

2. The process of claim 1 wherein the phenolic inhibitor is used at a concentration in the range of 500 to 1500 ppmw, based on the acrylic ester.

3. The process of claim 1 wherein the distillation is carried out in a distillation column operating at a bottom temperature in the range of 60–140° C.

4. The process of claim 3 wherein the distillation is carried out in a distillation column operating at a bottom temperature in the range of 80–110° C.

5. The process of claim 4 wherein the phenolic inhibitor is introduced into the distillation columns together with the acrylic ester containing stream.

6. The process of claim 4 wherein the phenolic inhibitor is introduced at or near the top of the distillation column.

7. The process of claim 4 wherein the oxygen is introduced at or near the bottom of the distillation column.

8. The process of claim 1 wherein the distillation is carried out in a cascade of distillation columns.

9. The process of claim 1 wherein the acrylic ester is methyl methacrylate.

10. A process for preparing a refined acrylic ester of general formula $CH_2=CR^1COOR^2$ wherein $R^1$ represents a hydrogen atom or an optionally substituted hydrocarbyl group and $R^2$ represents an optionally substituted hydrocarbyl group, the process comprising the step of distilling an acrylic ester containing stream comprising (i) an acrylic ester;

(ii) a homogeneous catalyst system for making acrylic ester from acetone cyanohydrin, ethene, propionic acid, propionaldehyde, methyl propionate or propyne, the catalyst system is based on: (a) Pd; (b) a mono- or bidentate phosphine ligand; and (c) a source of anions; and (iii) an alcohol in the presence of a phenolic inhibitor selected from the group consisting of hydroquinone and substituted hydroquinone, and the phenolic inhibitor is used at a concentration in the range of 200 to 5,000 ppmw, wherein the distillation is carried out in the presence of 0.001 to 1.0% v, on the vapor phase, of oxygen and wherein the distillation is carried out in two steps whereby in step (1) an azeotrope of the alcohol and acrylic ester is produced as a top product of a first distillation column, a bottom product from the first distillation column is introduced into a second distillation column where heavy ends and the residue of the catalyst system is removed from the refined acrylic ester from the bottom of said second distillation column and the refined acrylic ester is recovered over the top of said second distillation column.

11. The process of claim 10 wherein the alcohol is methanol.

12. The process of claim 10 wherein each step of the two step distillation set-up is carried out in a cascade of distillation columns.

* * * * *